United States Patent [19]

Patrick et al.

[11] Patent Number: 5,248,302
[45] Date of Patent: Sep. 28, 1993

[54] PERCUTANEOUS OBTURATABLE INTERNAL ANCHORING DEVICE

[75] Inventors: Algird Patrick, E. Brunswick; Ronald Marsh, Scotch Plains, both of N.J.

[73] Assignee: Biosearch Medical Products Inc., Somerville, N.J.

[21] Appl. No.: 925,967

[22] Filed: Aug. 5, 1992

[51] Int. Cl.⁵ ............................................ A61M 25/02
[52] U.S. Cl. .................................. 604/178; 604/105; 128/DIG. 26
[58] Field of Search ............... 604/174, 178, 177, 93, 604/103, 105, 106, 107, 264, 280, 247, 104; 128/DIG. 26

[56] References Cited

U.S. PATENT DOCUMENTS

| | | | |
|---|---|---|---|
| 781,763 | 2/1905 | Bowker | 604/105 |
| 1,870,942 | 8/1932 | Beatty | 604/105 |
| 3,397,699 | 8/1968 | Kohl | 604/105 |
| 3,799,172 | 3/1974 | Szpur | . |
| 3,815,608 | 6/1974 | Spinosa et al. | . |
| 4,140,119 | 2/1979 | Pollack | . |
| 4,393,873 | 7/1983 | Nawash et al. | 604/174 |
| 4,553,959 | 11/1985 | Hickey et al. | 604/96 |
| 4,573,576 | 3/1986 | Krol | 604/104 |
| 4,648,402 | 3/1987 | Santos | 128/345 |
| 4,660,571 | 4/1987 | Hess et al. | 128/784 |
| 4,666,433 | 5/1987 | Parks | 128/DIG. 26 |
| 4,680,029 | 7/1987 | Ranford et al. | 604/280 |
| 4,699,611 | 10/1987 | Bowden | 604/51 |
| 4,758,219 | 7/1988 | Sacks et al. | 604/105 |
| 4,781,682 | 11/1988 | Patel | 604/105 |
| 4,781,704 | 11/1989 | Potter | 604/270 |
| 4,798,592 | 1/1989 | Parks | 128/DIG. 26 |
| 4,808,163 | 2/1989 | Laub | 604/105 |
| 4,863,438 | 9/1989 | Gauderer et al. | 604/247 |
| 4,878,893 | 11/1989 | Chin | 604/21 |
| 4,921,485 | 5/1990 | Griffiths | 604/104 |
| 4,944,732 | 7/1990 | Russo | 604/247 |
| 5,073,166 | 12/1991 | Parks et al. | 604/174 |
| 5,122,122 | 6/1992 | Allgood | 604/105 |

OTHER PUBLICATIONS

Advertisement by Applied Medical Technology, Inc., undated.
Advertisement by C. R. Bard, Inc., undated.

Primary Examiner—John G. Weiss
Attorney, Agent, or Firm—Hoffmann & Baron

[57] ABSTRACT

An internal anchoring device to which a tubular member is attached for introduction/removal of fluids/gases into and out of viscera of a patient. The internal anchoring device is a discontinuous flexible body having a silhouette approximating a truncated pyramid when in a relaxed position. The internal anchoring device provides increased anchoring capability over devices of the prior art yet, at the same time, is easily obturated, thereby facilitating placement/removal.

17 Claims, 8 Drawing Sheets

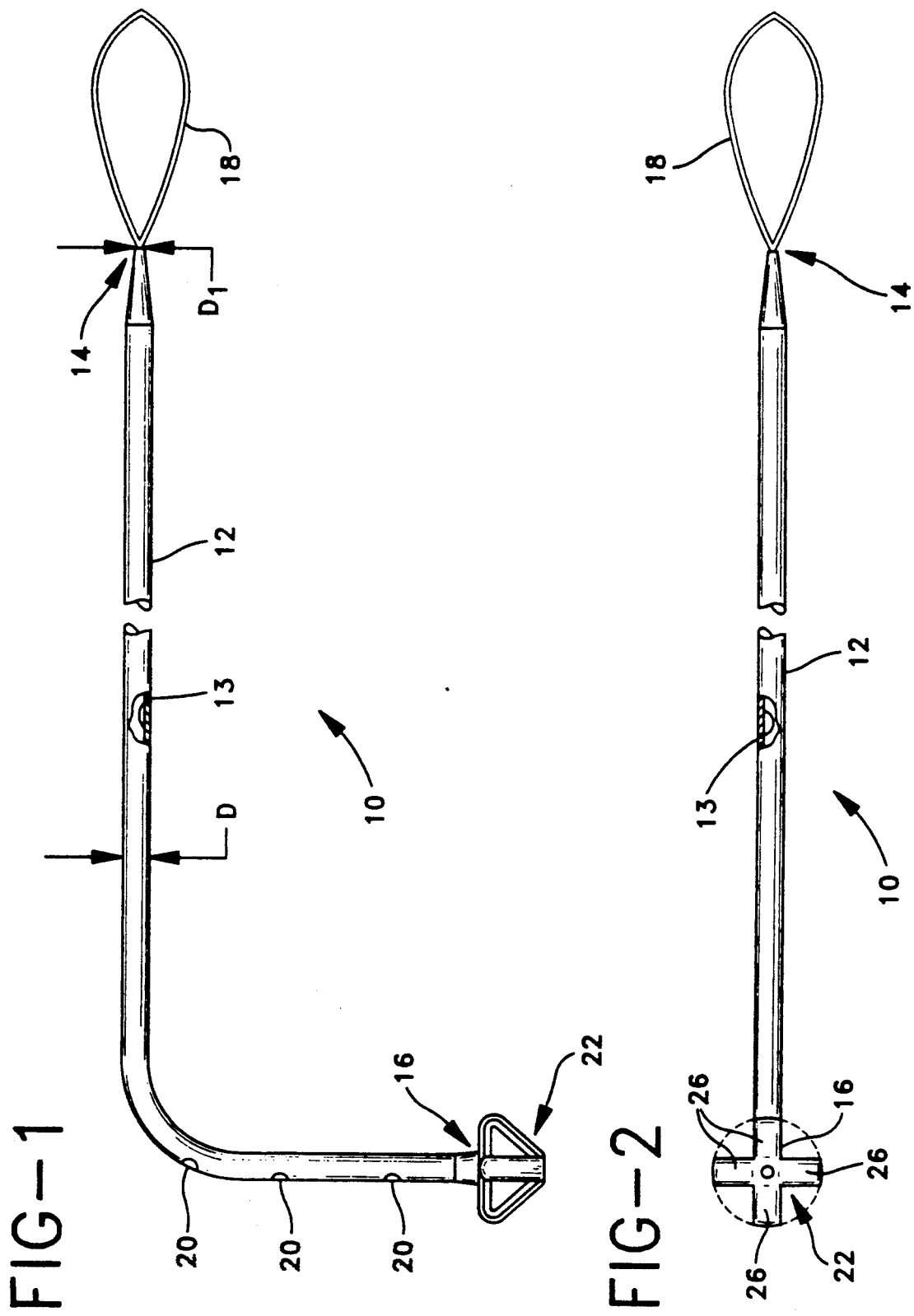

PERCUTANEOUS OBTURATABLE INTERNAL ANCHORING DEVICE

BACKGROUND OF THE INVENTION

The present invention relates to an internal anchoring device and, more particularly, to a percutaneous obturatable internal anchoring device for use with various gastrostomy tubes.

For example, numerous medical conditions exist in which it becomes necessary to gain percutaneous access to viscera such as the stomach. Situations where a patient has lost the ability to swallow and will require long term nutritional support may dictate feeding directly through the stomach. This type of feeding may be accomplished by inserting a feeding tube into the patient's stomach such that one end remains anchored in the stomach, while the other end remains external to the patients's body for connection to a nutrient source.

Feeding tubes may be inserted into a patient's stomach in a number of ways. One preferred method involves an endoscopic procedure whereby an endoscope is advanced through a patient's mouth, down the esophagus and into the stomach. A suture, which is inserted through a stoma in the abdomen wall, is attached to the endoscope. The endoscope is then withdrawn back up the esophagus and out of the patient's mouth. At this point, the suture is attached to a loop of filament wire included on the end of the feeding tube. The feeding tube is then "pulled" down the esophagus, into the stomach and out of the stoma in the abdomen wall.

Next, the physician grasps the tube and withdraws the remainder of the tube until the end of the tube, which includes some type of internal anchoring device, contacts the internal wall of the stomach. The anchoring device prevents the tube from being fully withdrawn from the stomach. The feeding tube is then secured to the individual by, for example, fitting a retention disk over the tube protruding outward from the stomach and positioning such disk into contact with the outer abdomen wall.

A feeding tube can also be placed into the stomach by "pushing" such tube down the esophagus over a previously-positioned guidewire. Moreover, a feeding tube or other gastrostomy tube may be positioned into the stomach through an existing stoma in the abdomen wall.

It is the design of the internal anchoring devices of the prior art that create many of the problems associated with gastrostomy tubes. For example, the anchoring capability of many of the prior art devices is less than desirable, resulting in inadvertent patient removal of the tube. Additionally, the anchoring device of the prior art units typically have a dome or mushroom shape, which provides a device with a relatively large profile, thus leading to patient discomfort or worse, hemorrhaging, during the removal procedure. Additionally, the prior art units are susceptible to clogging during introduction/removal of fluids/gases. Units having a mushroom-shaped anchoring device are particularly susceptible to clogging. Finally, the units of the prior art typically hinder the insertion and placement of auxiliary devices, e.g., jejunal tubes, which are inserted through the previously positioned gastrostomy tube and advanced into the small intestine.

SUMMARY OF THE INVENTION

The present invention, which addresses the problems associated with the prior art, is directed to a device designed to pass though an opening in the wall of the abdomen and stomach or other viscera of a patient and to be selectively operated between a relaxed retaining position and a flexed elongated position. The flexed elongated position allows the device to be inserted into and removed from the patient. The device includes a hollow tubular member having an inner end and an outer end and a longitudinal passage extending therethrough. The device also includes an anchoring device joined to the outer end of the tubular member. The anchoring device is a discontinuous flexible body having a silhouette approximating a truncated pyramid when in the relaxed position. The base of the pyramid is attached to the tubular member. The truncated apex of the pyramid has a guidance passage aligned with the longitudinal passage of the tubular member for directing, into the patient, a linear elongated body being advanced through the tubular passage. Finally, the device includes means for facilitating deformation of the flexible body from the relaxed position to the flexed elongated position formed interiorly of the truncated pyramid.

In a preferred embodiment of the present invention, the discontinuous flexible body includes a plurality of angularly-shaped retaining arms. Each of the arms includes a first segment extending generally perpendicularly from the tubular member and thereby forming the base of the pyramid. The arms also include a second segment joined to the first segment and extending to the truncated apex, thereby forming the sides of the pyramid. A preferred embodiment includes four arms spaced equidistantly about the perimeter of the tubular member.

As a result of the present invention, a percutaneous access device having increased anchoring capability over devices of the prior art is provided. Further, the device of the present invention, when obturated, has a much smaller profile than traditional dome or mushroom-shaped internal anchoring devices of the prior art, thereby reducing trauma and patient discomfort during the insertion/removal procedure. Additionally, the retaining arms of the present invention are formed with generous radii, which provide smooth, atraumatic surfaces such that necrosis is minimized as the device is inserted into the patient and positioned into place against the viscera wall. The design of the internal anchoring device of the present invention also reduces the risk of clogging during introduction/removal of fluids/gases. Finally, the design of the truncated apex of the internal anchoring device of the present invention facilitates the placement of auxiliary devices, e.g., jejunal tubes, endoscopes, etc.

BRIEF DESCRIPTION OF THE DRAWINGS

FIG. 1 is a side elevational view of a single pass percutaneous endoscopic gastrostomy feeding device employing the internal anchoring device of the present invention;

FIG. 2 is another side elevational view wherein the device shown in FIG. 1 has been rotated 90° out of the plane of FIG. 1.

FIG. 8a—8a is a cross-sectional view taken along lines 8a—8a;

DETAILED DESCRIPTION OF THE DRAWINGS

Figure 3:
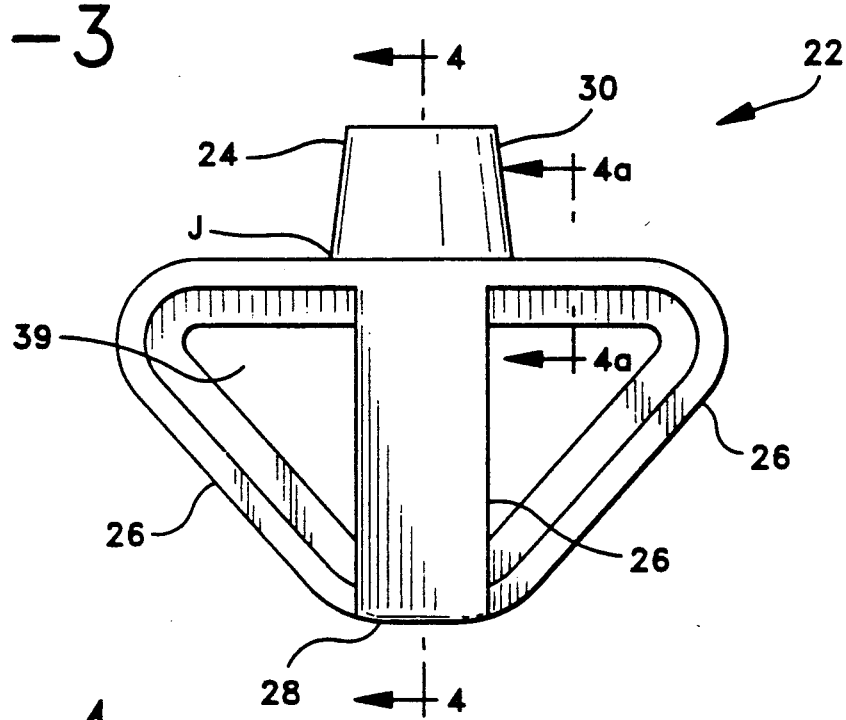
FIG. 3 is an enlarged detail of the internal anchoring device shown in FIG. 1.

Referring to the drawings, FIGS. 1 and 2 illustrate a single pass percutaneous endoscopic gastrostomy feeding device 10. Feeding device 10 includes a hollow tubular member 12 having a longitudinal passage 13 extending therethrough. Tubular member 12 has an outside diameter D. Tubular member 12 also includes a closed inner end 14 and an open outer end 16. Near inner end 14, the diameter of tubular member 12 tapers from D to $D_1$. A loop of filament wire 18 is attached to inner end 14. In this regard, feeding device 10 is sometimes referred to as a "pull-type" device.

As shown in FIG. 1, tubular member 12 is formed with a 90° bend near the outer end. This bend is included in the member for patient comfort. More specifically, by forming the tubular member with a 90° bend, the majority of the tube, once such tube is positioned in the body, will "dangle" outside of the patient parallel to the body, thereby reducing to a minimum the unsightly and uncomfortable situation created by those devices which protrude horizontally outwards from a patient. Although it is possible to bend the tube after it has been placed in the body, this creates unnecessary stresses in the tube that may serve to weaken such device. The 90° bend in the tube also tends to reduce the possibility of pressure necrosis.

After the tube is positioned in the patient, the tube is cut to remove the inner end, along with the loop of filament wire. The tube is cut so that approximately 2 to 6 inches of the tube "dangles" from the patient's body. A sealable fitting is then connected to this newly-created inner end.

Tubular member 12 includes a plurality of graduations 20 for determining the distance of insertion into the patient. Graduations 20 are located longitudinally on the outside surface of tubular member 12.

Attached to outer end 16 is an internal anchoring device 22 operable between a relaxed retaining position and a flexed elongated position. The internal anchoring device is a discontinuous flexible body having a silhouette approximating a truncated pyramid when in the relaxed position. (Internal anchoring device 22 is shown in the relaxed position in FIGS. 1-6, 9a and 10-11).

Figure 4:
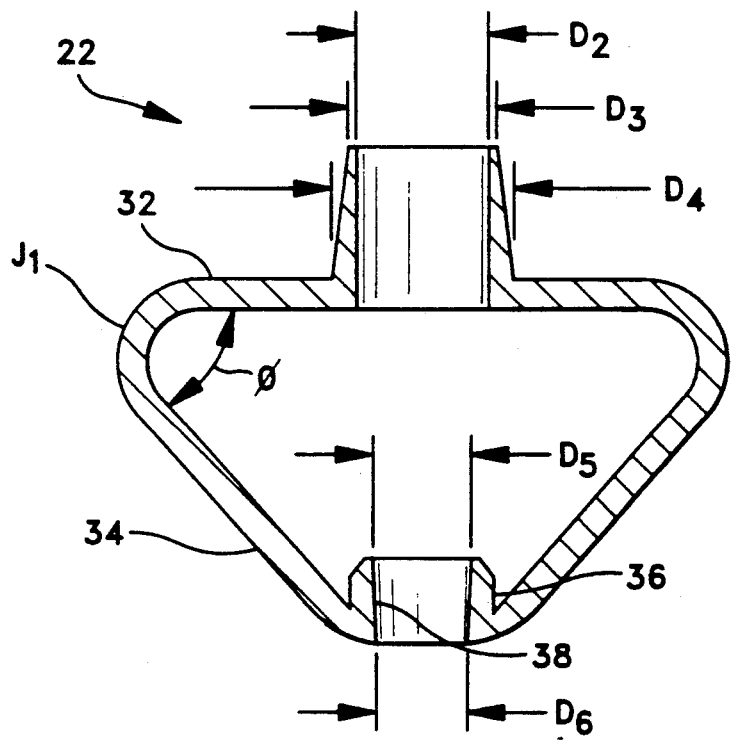
FIG. 4 is a cross-sectional view taken along lines 4—4 of FIG. 3.

As best shown in FIGS. 3 and 4, the truncated pyramid includes a base 24, a plurality of angularly-shaped retaining arms 26 and a truncated apex 28. The retaining arms connect base 24 to truncated apex 28.

Base 24 includes a sleeve 30 having a constant inside diameter $D_2$. Outside diameter D of tubular member 12 is sized such that tubular member 12 will slide within sleeve 30. In a preferred embodiment, internal anchoring device 22 is bonded to tubular member 12. As best shown in FIG. 4, the outside circumference of sleeve 30 increases in diameter from $D_3$ to $D_4$, thereby a strong joint at juncture J of sleeve 30 and retaining arms 26.

Figure 4A:
FIG. 4a is a cross-sectional view taken along lines 4a—4a of FIG. 3.

A preferred embodiment of the present invention includes four retaining arms 26 spaced equidistantly about the perimeter of tubular member 12. Each of these retaining arms includes arm segments 32,34. Arm segment 32 extend generally perpendicularly from the tubular member and form the base of the truncated pyramid. Arm segment 34 extend from arm segment 32 to truncated apex 28 and thereby form the sides of the truncated pyramid. Arm segments 32 meets arm segments 34 at juncture $J_1$, and create interior angle $\phi$. Angle $\phi$ is on the order of from about 40°-60° and, preferably, is about 50°. As shown in FIG. 4a, arm segments 32 are formed with generous radii, i.e., they have a curvilinear cross-section. Arm segments 34 are formed with a similar curvilinear cross-section. The curvilinear cross-sections preferably have a radius of from about ¼ inch to about ¾ inch and, more preferably, of about ½ inch.

Truncated apex 28 includes angular collar 36. Truncated apex 28 also includes a passage 38, which tapers from a diameter $D_5$ to a diameter $D_6$. Passage 38 is aligned with longitudinal passage 13.

As previously mentioned, a preferred embodiment of the present invention employs four retaining arms. The use of four retaining arms provides better anchoring capability than devices of the prior art having fewer arms. In addition to reducing the possibility of inadvertent removal, the use of four retaining arms enhances the process of securing the stomach wall to the abdominal wall.

Moreover, the configuration of the retaining arms provides four wedge-shaped openings 39 through which fluids exiting the tubular member may enter the body. In contrast to the mushroom-shaped retention heads of the prior art, the design of the present invention reduces the risk of having the internal retention device clog during feeding. Additionally, the present design increases the amount of open area for gastric decompression.

Feeding device 10 may be inserted by a standard endoscopic procedure whereby the feeding device is advanced through an individual's mouth, passed through the esophagus and into the individual's stomach. In this regard, the edges of the four retaining arms, which are molded with generous radii as described above, facilitate insertion into and removal from a patient. The curvilinear cross-section provides a smooth, atraumatic surface, which, in turn, minimize tissue trauma as the feeding device is passed through the esophagus and positioned into place. Additionally, the curvilinear cross-section allows the internal retention device to cradle against the stomach wall of a patient, thereby minimizing trauma.

Figure 5:
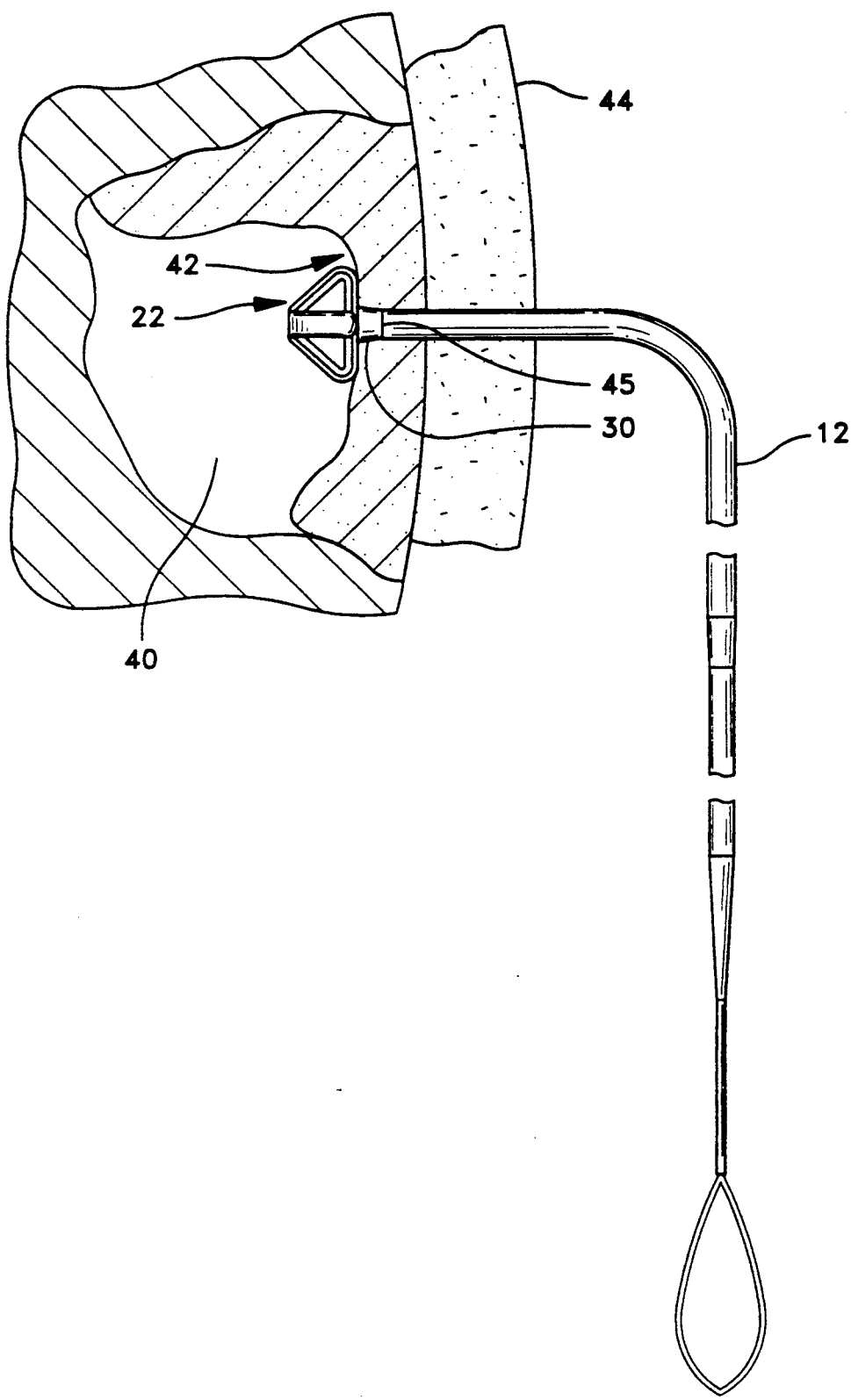
FIG. 5 is a view, in partial section, of a feeding device employing the internal anchoring device of the present invention positioned within the stomach of an individual.

Referring now to FIG. 5, feeding device 10 is shown positioned within a stomach 40. Internal anchoring device 22 abuts stomach wall 42 and prevents withdrawal of the feeding device. As may be readily understood, the taper of sleeve 30 facilitates the placement of the feeding device. In other words, by tapering sleeve 30 from $D_4$ to $D_3$, the outside diameter of sleeve 30 becomes approximately equal to outside diameter D of tubular member 12. As a result, shoulder 45 is minimized and does not "catch" stomach wall 42 as the feeding device is drawn outwards. The taper from D4 to D3 also serves to "plug" the stoma, thereby preventing leakage.

Figure 6:
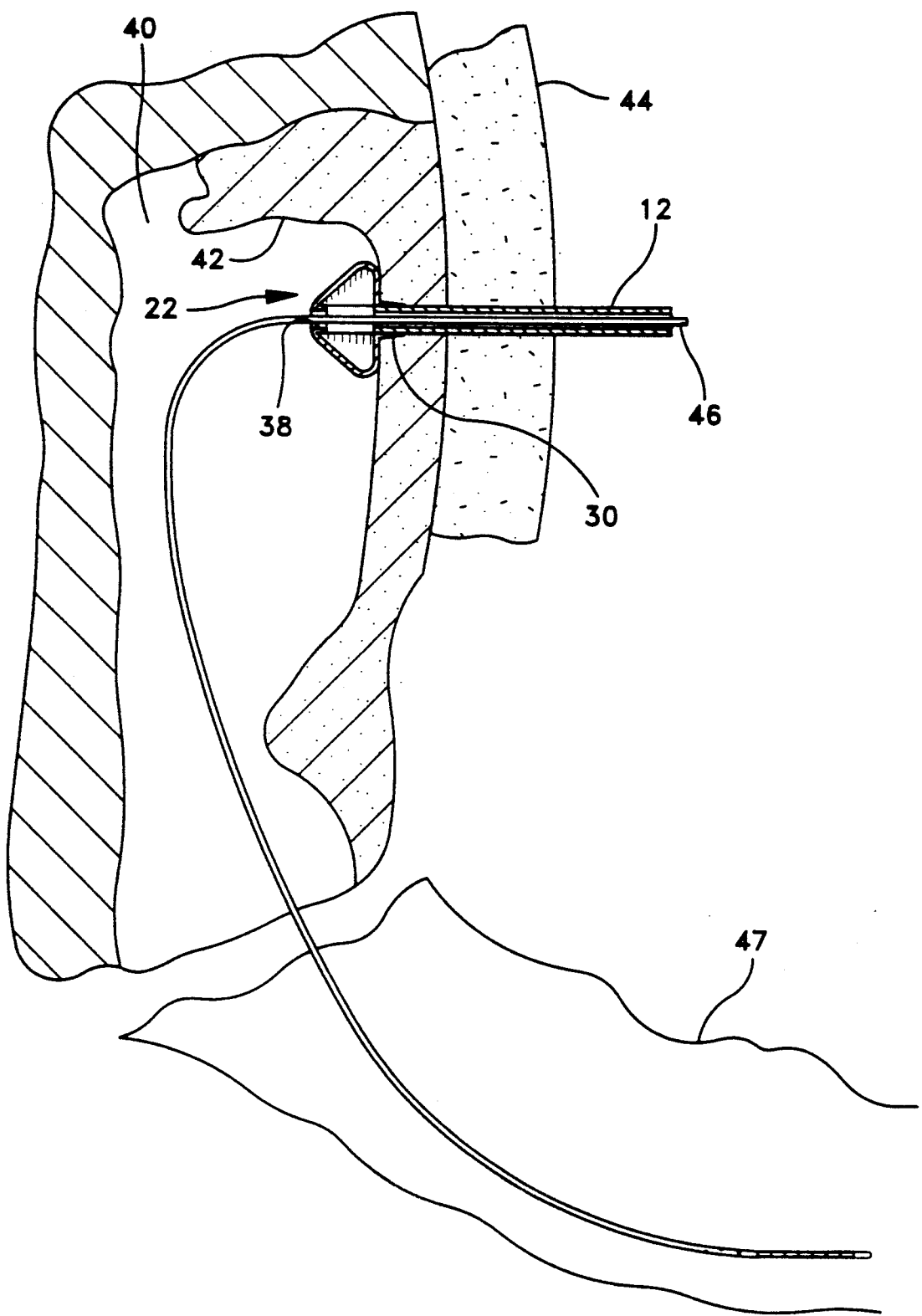
FIG. 6 is a view, in partial section, showing an auxiliary feeding tube inserted through a feeding device employing the internal anchoring device of the present invention and into the small intestine.

Referring to FIG. 6, the design of the present invention facilitates the placement of an auxiliary device 46, e.g., a jejunal tube, which may be used to feed to a predetermined location in small intestine 47. Unlike the prior art device which typically only have openings along their sides, internal retention device 22 includes passage 38 which greatly enhances the ability to place the auxiliary device. Specifically, passage 38 allows the auxiliary device to be advanced along a straight line directly into the stomach. The taper of passage 38 guides the auxiliary device exiting sleeve 30 into the passage. Once the auxiliary device is passed through passage 38 of internal retention device 22, it may then easily be advanced into the individual's intestine.

Although endoscopic procedures are typically preferred over surgical procedures (surgical procedures are more invasive and often require the use of a general anesthetic whereas endoscopic procedures do not), there is still a degree of discomfort and psychological stress involved with such a procedure. Accordingly, it would be desirable to be able to remove the feeding device, once it had been positioned in the stomach, without the need of performing a second endoscopic or surgical procedure. In this regard, there is typically a trade-off between anchoring capability and ability to remove the feeding device without performing a second endoscopic procedure (i.e., percutaneous removal). More specifically, those devices of the prior art which are able to be removed percutaneously often have limited anchoring capability, while those devices with good anchoring capability often require a second endoscopic procedure for removal. The present invention provides an ideal design in that it offers good anchoring capability yet, at the same time, allows for atraumatic percutaneous removal. An additional embodiment allows for atraumatic placement of such device.

Figure 7:
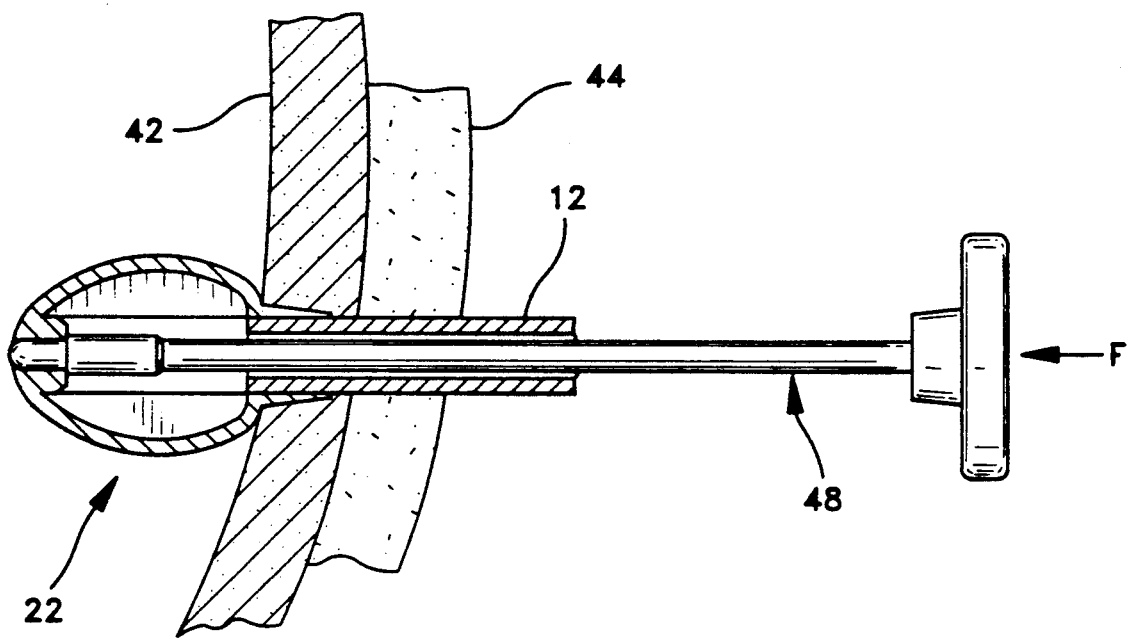
FIG. 7 is a view, in partial section, of a feeding device employing the internal anchoring device of the present invention obturated for placement/removal.

This result is accomplished through the inventive configuration of retaining arms 26, together with the design of truncated apex 28. More specifically, each of retaining arms 26 is configured as two independent, yet cooperating, arm segments 32 and 34. Internal anchoring device 22 may therefore be easily elongated since arm segments 32 and 34 provide little or no resistance to a force F (see FIG. 7) applied along the longitudinal axis of the feeding device. The internal anchoring device is shown in the flexed elongated position in FIG. 7. It is in this position that the internal anchoring device may be inserted into and removed from a patient.

Figure 8:
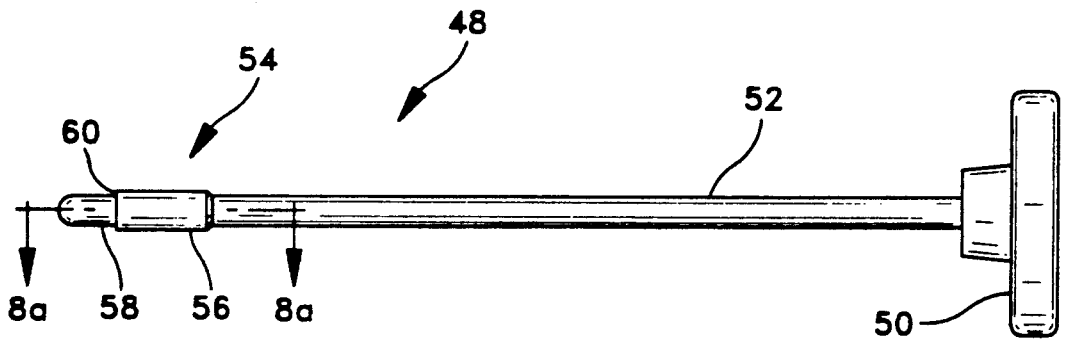
FIG. 8 is a view of an obturator used in accordance with the present invention.
Figure 8A:
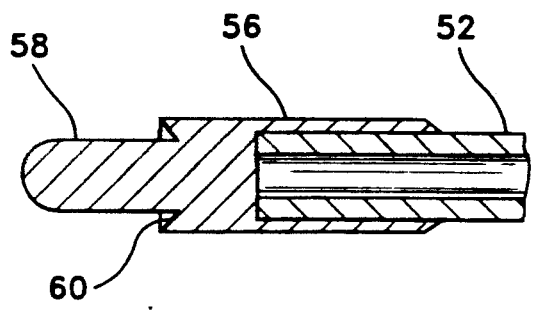

In detail, the internal anchoring device is flexibly elongated by means of an obturator 48, as shown in FIGS. 8 and 8a. Obturator 48 includes a thumb ring 50, a rod 52 and an obturating end 54. Obturating end 54 is formed with an enlarged neck 56 and a tapered tip 58. An angular shoulder 60 is formed at the junction of neck 56 and tip 58.

Figure 9A:
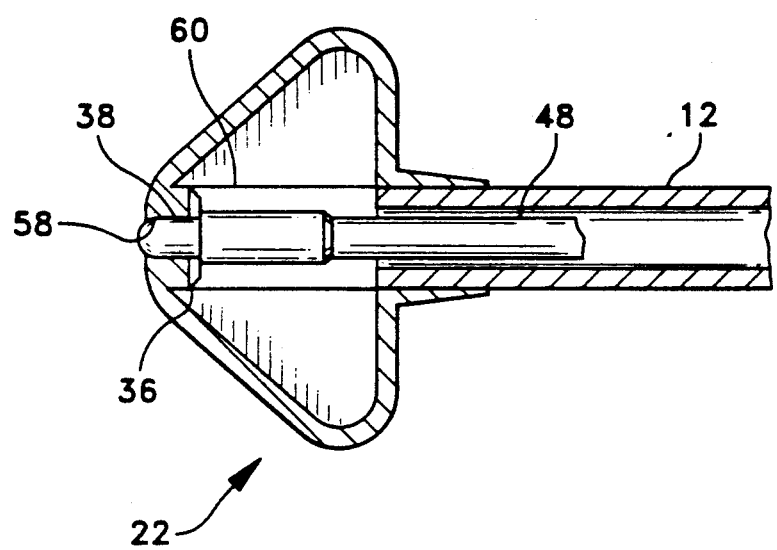
FIG. 9a is an enlarged cross-sectional view showing the obturator positioned within the internal anchoring device of the present invention.
Figure 9B:
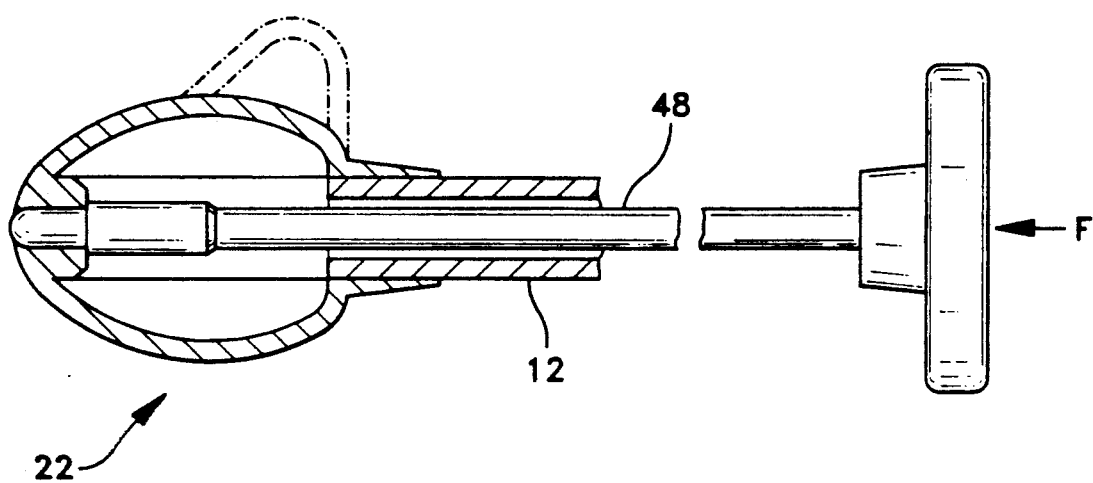
FIG. 9b is an enlarged cross-sectional view showing the internal anchoring device of the present invention obturated for placement/removal.

Referring to FIGS. 9a and 9b, the taper of tip 58 is configured to correspond with the taper of passage 38. In use, obturator 48 is inserted through tubular member 12 until tip 58 slides within passage 38. Tip 58 slides within passage 38 until angular shoulder 60 contacts angular collar 36. This design ensures a snug fit between the obturating end of the obturator and the internal retention device. In turn, this prevents an inadvertent slippage of the obturator through passage 38 during the placement/removal procedure, which would allow the retention members to expand to their normal shape and cause discomfort, or possibly injury, to the patient.

By applying a force F, as shown in FIG. 9b, the internal anchoring device is obturated, i.e., elongated. When obturated, the internal anchoring device of the present invention has a significantly smaller profile than the traditional dome or mushroom-shaped heads of the prior art devices. A small profile helps to reduce friction and patient discomfort as the feeding device is percutaneously placed/removed from the patient. The present invention provides this desirable feature without sacrificing anchoring capability.

Figure 10:
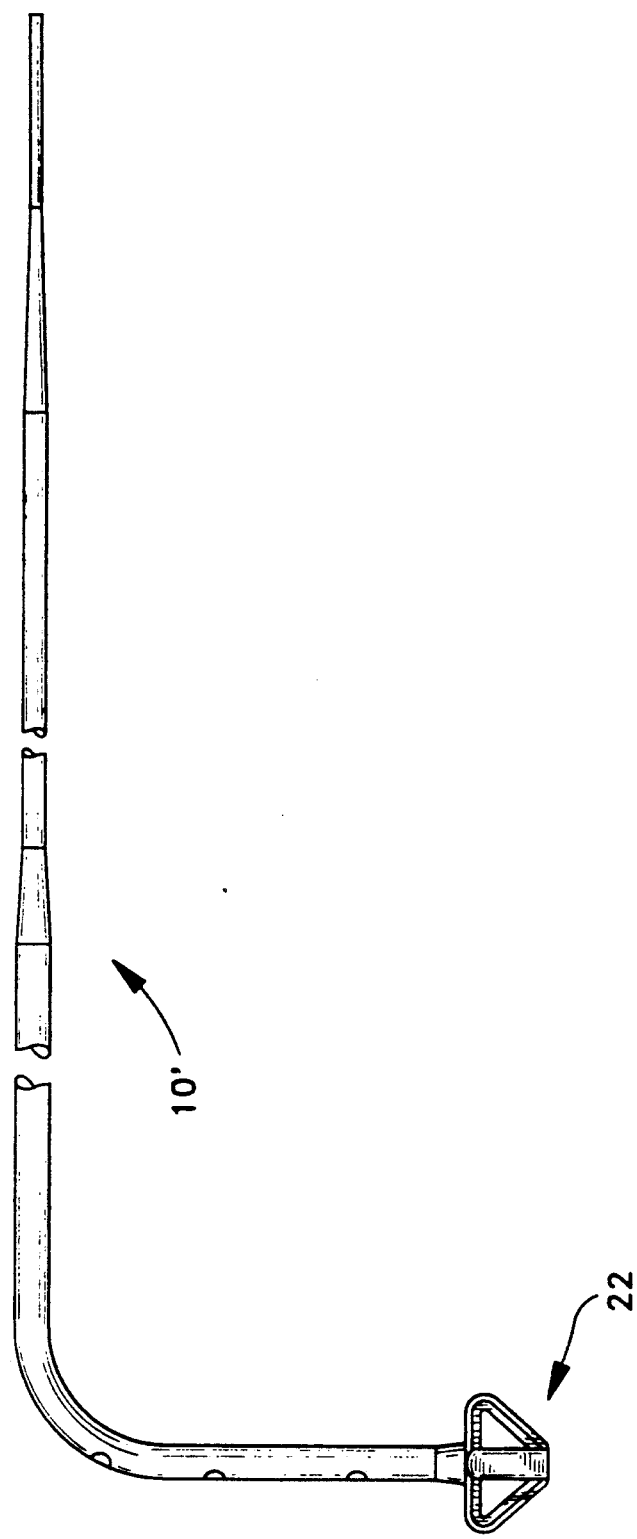
FIGS. 10 and 11 are side elevational views of alternative devices employing the internal anchoring device of the present invention.

It is also feasible for a feeding tube employing the present invention to be inserted into the stomach over a guidewire. In this situation, an alternative embodiment of the feeding device, e.g., feeding device 10' shown in FIG. 10, may be employed. Feeding device 10 is referred to as a "push-type" device. Because feeding device 10' is inserted into the stomach over a guidewire, the loop of filament wire, as used in feeding device 10, is not required. Feeding device 10' is depicted in FIG. 10 with an elongated inner end; however, the device may also be formed with an inner end similar in configuration to that shown in FIGS. 1 and 2. In all other respects, feeding device 10' is similar to feeding device 10.

Figure 11:
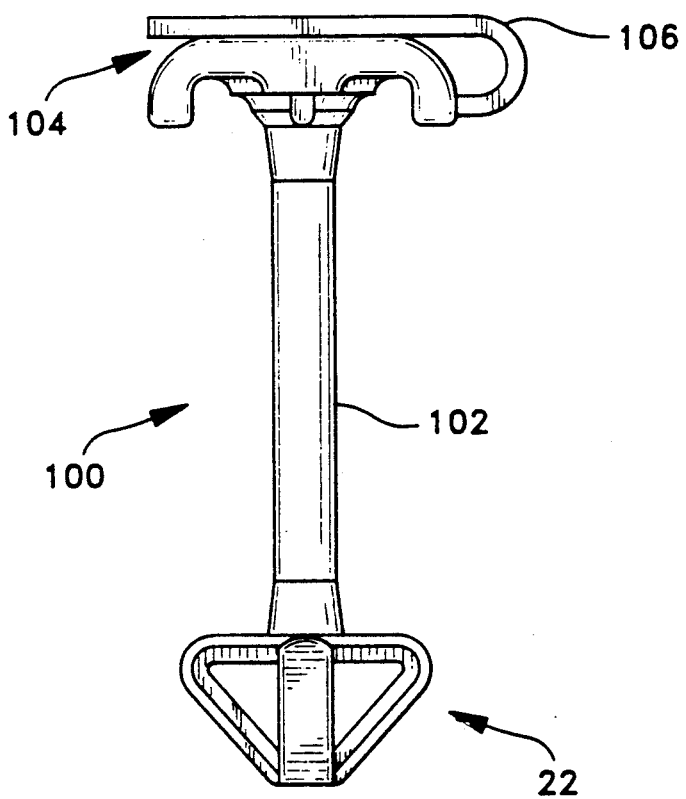

Referring to FIG. 11, the anchoring device of the present invention may also be employed with a medical device, e.g., a low-profile gastrostomy tube 100, for insertion directly into the stomach or other viscera through an existing stoma. Gastrostomy tube 100 includes internal anchoring device 22, which is connected to the outer end of a tubular member 102. Connected to the inner end of tubular member 102 is a sealable "flip-type" cap fitting 104. Cap fitting 104 includes an attached cap 106, which when removed from the cap fitting allows access to the tube for both introduction/removal of fluids/gases and for insertion of the obturator for placement/removal.

While there have been described what are presently believed to be the preferred embodiments of the invention, those skilled in the art will realize that various changes and modifications may be made to the invention without departing from the spirit of the invention, and it is intended to claim all such changes and modifications as fall within the scope of the invention.

What is claimed is:

1. A device designed to pass through an opening in the wall of the abdomen and stomach or other viscera of a patient and to be selectively operated between a relaxed retaining position and a flexed elongated position for insertion into and removal from said patient, said device comprising:

a hollow tubular member having an inner end and an outer end and a longitudinal passage extending therethrough;

an anchoring device joined to said outer end, said anchoring device having a discontinuous flexible body with a silhouette approximating a truncated pyramid in the relaxed position, the base of said pyramid attached to said tubular member and the truncated apex of said pyramid having a guidance passage aligned with said longitudinal passage for directing a linear elongated body being advanced through said tubular member into said patient; and means for facilitating deformation of said flexible body from said relaxed position to said flexed elongated position formed interiorly of said truncated pyramid.

2. The device according to claim 1, wherein said discontinuous flexible body comprises a plurality of angularly-shaped retaining arms, each of said arms having a first segment extending generally perpendicularly from said tubular member and forming said base of said pyramid, and a second segment extending from said first segment to said truncated apex and joined thereto to form the sides of said pyramid.

3. The device according to claim 2, wherein said first and second arm segments form an angle of from about 40° to about 60° in the relaxed position.

4. The device according to claim 3, wherein said first and second arm segments form an angle of 50° in the relaxed position.

5. The device according to claim 2, wherein each of said arms has a curvilinear cross-section to facilitate insertion into and removal from a patient and to cradle against the viscera wall of said patient to minimize trauma.

6. The device according to claim 5, wherein said cross-section is an arc of a circle having radii of from about ¼ inch to about ¾ inch.

7. The device according to claim 6, wherein said cross-section is an arc of a circle having a radius of ½ inch.

8. The device according to claim 1, wherein said anchoring device is a separate component which further comprises a sleeve extending from said base of said pyramid and sized for connection to said outer end of said tube.

9. The device according to claim 1, wherein said inner end of said tubular member further comprises an extension with a reduced cross-section and a means for withdrawing said tubular member through the viscera of said patient.

10. The device according claim 9, wherein said means for withdrawing is a loop of strand material.

11. The device according claim 9, wherein said strand material is selected from the group consisting of wire, thread and plastic filament.

12. The device according to claim 1, wherein said inner end of said tubular member further comprises an extension configured to pass over a guide wire.

13. The device according to claim 1, wherein said tubular member further comprises graduated indicia on the outer surface to indicate length of tube insertion into said patient.

14. The device according to claim 9, wherein said tubular member is formed with an approximately 90° bend.

15. The device according to claim 14, wherein said 90° bend is formed in said tubular member at a distance of from about 2 to about 4 inches from said outer end.

16. The device according to claim 1, further comprising a sealable cap fitting connected to said inner end.

17. The device according to claim 16, wherein said cap fitting includes an attached cap which when removed from said fitting allows access to said viscera of said patient.

* * * * *